US009278171B2

(12) United States Patent
Brandl et al.

(10) Patent No.: US 9,278,171 B2
(45) Date of Patent: Mar. 8, 2016

(54) METHOD FOR DETECTING THE ION CONCENTRATIONS OF CITRATE ANTI-COAGULATED EXTRACORPOREAL BLOOD PURIFICATION

(75) Inventors: Martin Brandl, Spitz (AT); Jens Hartmann, Furth (AT); Karin Strobl, Strass (AT); Dieter Falkenhagen, Krems (AT)

(73) Assignee: Zentrum fur Biomedizinische Technologie der Donau-Universitat Krems, Krems (AT)

( * ) Notice: Subject to any disclaimer, the term of this patent is extended or adjusted under 35 U.S.C. 154(b) by 1649 days.

(21) Appl. No.: 12/675,605

(22) PCT Filed: Aug. 28, 2008

(86) PCT No.: PCT/AT2008/000305
§ 371 (c)(1),
(2), (4) Date: Apr. 18, 2011

(87) PCT Pub. No.: WO2009/026603
PCT Pub. Date: Mar. 5, 2009

(65) Prior Publication Data
US 2011/0208105 A1 Aug. 25, 2011

(30) Foreign Application Priority Data

Aug. 31, 2007 (AT) .................................. 1368/2007

(51) Int. Cl.
*A61M 1/34* (2006.01)
*A61M 1/36* (2006.01)
*A61M 37/00* (2006.01)

(52) U.S. Cl.
CPC .............. *A61M 1/342* (2013.01); *A61M 1/3672* (2013.01); *A61M 1/3675* (2013.01); *A61M 2205/33* (2013.01)

(58) Field of Classification Search
CPC . A61M 1/342; A61M 1/3441; A61M 1/3445; A61M 1/3462; A61M 1/36; A61M 37/00
USPC ............................... 604/6.06, 6.11, 5.01, 4.01
See application file for complete search history.

(56) References Cited

U.S. PATENT DOCUMENTS

| 7,373,195 B2* | 5/2008 | Ye .................................. 600/348 |
| 8,211,048 B2* | 7/2012 | Szamosfalvi et al. ................... A61M 1/3672 210/646 |
| 2005/0006296 A1* | 1/2005 | Sullivan et al. ............ 210/321.6 |
| 2007/0066928 A1* | 3/2007 | Lannoy ........................ 604/6.07 |

* cited by examiner

*Primary Examiner* — Tatyana Zalukaeva
*Assistant Examiner* — Ilya Treyger
(74) *Attorney, Agent, or Firm* — KPPB LLP

(57) ABSTRACT

The invention relates to a device for the citrate anti-coagulated extracorporeal blood purification comprising:
an extracorporeal blood purification system comprising an extracorporeal blood circuit (202), which comprises a dialysis unit (205), a blood inflow (203) and a blood discharge (204), a citrate metering device (212) for supplying citrate at a citrate supply point (213) upstream of the dialysis unit (205), a substitution medium metering device (214) for supplying a substitution medium at a substitution medium supply point (215) downstream from the dialysis unit (205), at least one ion concentration measuring means (224) for measuring bivalent cations and a controller (225), wherein the controller (225) is adapted to regulate the metering of the substitution medium as a function of a comparison between a setpoint value range and the ion concentration measured by means of the ion concentration measuring means (224), wherein the ion concentration measuring means (224) is adapted for the continuous generation of measuring values and is arranged upstream of the citrate supply point (213) and the controller (225) is adapted to continuously carry out a regulation of the metering of the citrate and of the substitution medium in consideration of a target value or target value range, which can be predetermined in the controller (225) downstream from the citrate supply point (213). The invention further relates to a method for detecting the ion concentration.

15 Claims, 7 Drawing Sheets

FIG.1(state of the art)

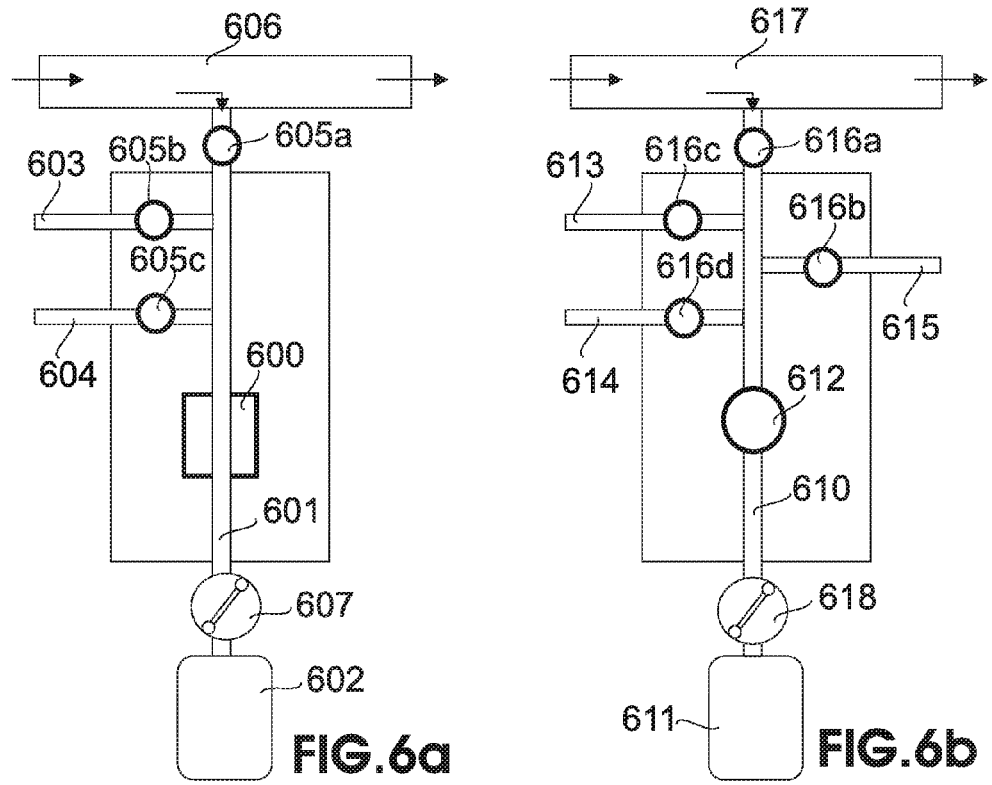
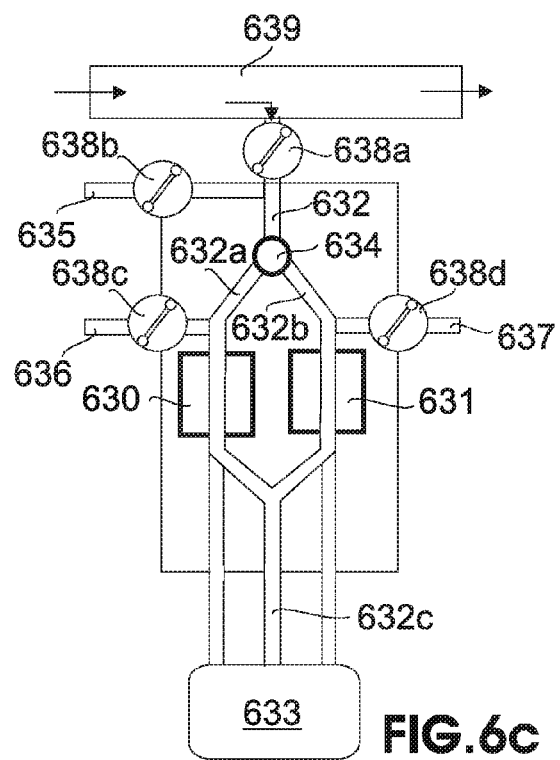

METHOD FOR DETECTING THE ION CONCENTRATIONS OF CITRATE ANTI-COAGULATED EXTRACORPOREAL BLOOD PURIFICATION

CROSS-REFERENCE TO RELATED APPLICATION

The current invention claims priority to PCT application number PCT/AT2008/000305, filed Aug. 28, 2008, and Austrian patent application number A1368-2007, filed Aug. 31, 2007, the disclosures of each of which are incorporated herein by reference.

FIELD OF THE INVENTION

The invention relates to a device for citrate anti-coagulated extracorporeal blood purification comprising: an extracorporeal blood purification system comprising a extracorporeal blood circuit, which comprises a dialysis unit, a blood inflow to the dialysis unit for blood drawn from a patient and a blood discharge from the dialysis unit for blood, which is to be returned into the patient, a controlled citrate metering device for supplying citrate to a citrate supply point upstream of the dialysis unit, a controlled substitution medium metering device for supplying a substitution medium to a substitution supply point downstream from the dialysis unit, at least one ion concentration measuring means for measuring bivalent cations and a controller, which is connected to the at least one ion concentration measuring means as well as to the citrate metering device and to the substitution medium metering device, wherein the controller is adapted to regulate the metering of the substitution medium as a function of a comparison between a setpoint value range and the ion concentration measured by means of the ion concentration measuring means.

The invention further relates to a method for detecting an ion concentration of bivalent cations of the blood during a citrate anti-coagulated extracorporeal blood purification, in the case of which a substitution medium is introduced into an extracorporeal blood circuit at an extracorporeal blood circuit on a citrate supply point, which is located upstream of a dialysis unit, and at a substitution medium supply point, which is located downstream from the dialysis unit, and the controlling of the metering of the substitution medium is carried out as a function of a comparison between a setpoint value range and the measured ion concentration.

BACKGROUND OF THE INVENTION

A blocking of blood clotting is required in most patients requiring an extracorporeal blood purification. The contact of blood or plasma, respectively, to foreign surfaces leads to contact activation and subsequently to clotting, release of quinines and to the activation of the complement system. These processes are also triggered by extracorporeal blood purification methods, because plasma or blood, respectively, in the context of these methods is brought into contact with membranes and possibly with adsorber materials. Due to the high demands on patient safety and the high prevalence for blood-purifying therapies, a safe, effective and easily manageable anti-coagulation is essential.

In the clinical treatment of hemodialysis patients, heparin, which is introduced into the arterial branch of the extracorporeal blood circuit by means of infusion, is used as current standard. Heparin, however, can lead to complications, such as, e.g., HIT (Heparin Induced Thrombocytopenia), [Hetzel G R, Sucker C (2005), Nephrol Dial Transplant, 20 (10): 2036-2042; M. Franchini (2005), Thrombosis Journal, 3 (14)], heparin bond to the adsorber or filter or an undesired intracorporeal anti-coagulation, wherein the latter can become problematic in particular in the case of patients having an increased risk of bleeding.

The anti-coagulation with citrate [Janssen M] et al. (1993), Nephrol Dial Transplant, 8 (11): 1228-1233; Pinnick et al. (1983), N Engl J Med, Vol. 308, 258-261] represents an alternative to the heparin method. The anti-coagulatory effect of the citrate is based on the complex formation thereof with free bivalent cations, such as calcium ions and magnesium ions. Ionized calcium is an important cofactor in the clotting system, because it has a catalytic effect on most of the enzymes of the clotting cascade. A complexation of the calcium ions by means of citrate thus leads to a prevention of the development of the clotting cascade. Used concentrations reach from 2 to 7.4 mmol citrate per liter of blood [Palsson R, Niles J L (1999), Kidney Int 55: 1991-1997; Böhler et al. (1996), J Am Soc of Nephrol. 7(2), 234-241], wherein concentrations of the ionized calcium are specified from 0.25 mmol/l to 0.35 mmol/l as target values [Kutsogiannis et al. (2000), Am J Kidney Dis, Vol. 35, 802-811; Tolwani et al. (2001), Kidney International, Vol. 60, 370-374] or <0.4 mmol/l [Swartz et al. (2004), Clinical Nephrology, Vol. 61(2), 134-14], respectively, as target values.

An extracorporeal blood circuit substantially consists of a filter unit, a blood inflow from the patient to the filter unit (arterial branch) and a blood discharge from the filter unit to the patient (venous branch). The blood is pumped through the circuit by means of a blood pump. As described below, the blood flow [ml/min] is an important parameter for the system and represents the blood volume, which is pumped by the blood pump per time unit. The filter unit typically includes a dialysis filter, a plasma filter or a hemofilter, respectively, or a combination thereof. The membrane blood purification methods are based on the physical processes of diffusion and convection. A semi-permeable membrane, which separates the blood from the dialysis liquid, is located in the dialysis filter. Low-molecular substances thereby diffuse from the blood into the dialysis liquid and are thus removed from the blood. The extent of the removal of the substances is called clearance and is a function of the dialysis filter as well as of the blood and dialysis flow. In the case of dialysis, liquid accumulated in the body can also be removed from the patient by means of transmembrane pressure. This process is also called ultrafiltration. In the case of the hemofiltration, filtrate is pressed out at an ultrafiltration membrane and is replaced by substitution solution. Depending on the used filter, the filtrate includes low-molecular or low- and high-molecular substances. In the case of a further known blood purification method, filtrate is pressed out via a hemo- or plasmafilter and is recirculated in a plasma circuit, is cleaned (e.g. by means of adsorbers or by means of MDS—Microspheres Detoxification System [EP 0776223, U.S. Pat. No. 5,855,782] and is subsequently returned into the extracorporeal blood circuit. In addition to the membrane blood purification systems, there are adsorption systems, in the case of which the blood or the plasma passes through an adsorber and is cleaned by means of physicochemical processes. Typically, an adsorber consists of an active matrix, which specifically removes undesired blood components from the blood. It goes without saying that the citrate anti-coagulation is also suitable for adsorber systems. However, a dialysis filter is advantageously arranged downstream from the adsorber circuit so as to partially remove the citrate from the blood circuit prior to the reinfusion of the blood, as will be described below.

The citrate supply takes place by means of an infusion into the arterial branch of the extracorporeal blood circuit. The blood, which is blocked from clotting in such a manner, is cleaned in membrane or membrane/adsorption-based systems, respectively. The citrate as well as the citrate-calcium complex is again removed for the most part from the extracorporeal blood circuit by means of the dialysis as a function of the used dialysis filter, so that only a small portion of the infused citrate reaches into the blood circuit of the patient. A dialysis unit is thus advantageous for the citrate anti-coagulation. Citrate is metabolized to $CO_2$ and water in the human body, wherein the citrate impact on the patient may not considerably exceed the metabolic rate, so as to prevent a pathophysiologically relevant impact on the acid-base balance. So as not to change the clotting system and other physiological functions of calcium and magnesium ions in the patient, a substitution of these ions is necessary. A calcium-containing or a calcium and magnesium-containing substitution medium is thereby introduced into the blood either by infusion into the venous branch of the extracorporeal blood circuit or via a separate vein access.

The most important therapeutic advantage of the citrate anti-coagulation lies in that—contrary to the heparin anti-coagulation—the blood clotting is exclusively blocked in the extracorporeal circuit and undesired intracorporeal bleedings are thus avoided. In addition to the anti-coagulation, a citrate addition considerably improves the biocompatibility of an extracorporeal blood purification system, because the complement activation, which requires the presence of free calcium and magnesium ions, is suppressed by the complexation of these ions. The citrate anti-coagulation can further be used in patients, in the case of whom heparin anti-coagulation is contraindicated (HIT). Due to extended filter lives in response to the use of citrate anti-coagulation, this is particularly suitable for long-term treatments, such as in the acute dialysis, e.g.

Even though the advantages of the citrate anti-coagulation as compared to the heparin standard method are obvious, it is only rarely used in the clinical treatment and only in a few blood purification devices. The following reasons explain why the method has not yet prevailed despite of its advantages for the patient: on the one hand, the citrate anti-coagulation is slightly more extensive than the heparin method and, on the other hand, it is associated with a safety risk due to the complexity of the metering and the lack of automation and standardization, it requires a careful monitoring and is thus consequently only carried out by experienced experts. In response to changes to the extracorporeal blood flow, the supply rates for citrate and for the substitution medium must be adapted manually. An incorrect metering, which is caused, for example, by means of an operating error, an incorrect adjustment of the supply rates or an infusion pump breakdown, can lead to complications, such a hypocalcaemia. This is a state, which can take on life-threatening extents. The metering should be adjusted by means of the detected ion concentration of the patient blood—advantageously of the calcium ion concentration. The risk of an undesired unphysiological state can be minimized and the safety of the patient can be ensured only by means of the most accurate as well as highly close-meshed or continuous measuring of the calcium ion concentration of the blood, which causes a likewise close-meshed or continuous adaptation of the metering of the infusion solutions. In consideration of the necessity for an anti-coagulation system, which is also suitable for patients, for whom a use of the heparin method is disadvantageous or not possible, and in consideration of the advancing aging of the population and the increasing prevalence for blood-purifying therapies connected thereto, there is thus a large demand for a reliable and effective as well as automated and standardized citrate anti-coagulation system, by means of which the patient safety can be kept as high as possible.

WO 91/06326 presents a dialysis method with citrate anti-coagulation for the use in hemodialysis. The citrate is infused into the arterial branch of the extracorporeal blood circuit, wherein the citrate supply rate is adjusted as a function of the blood flow rate. Calcium ions are substituted via a separate venous access, wherein the supply rate of the Ca-ion substitution solution is adjusted by means of the citrate supply rate and of the Ca-ion concentration of drawn blood samples detected over time intervals lasting for several hours. A close-meshed or continuous monitoring of the Ca-ion concentration, respectively, does not take place in the method described in WO 91/06326 and as already specified above, the safety of the patient can thus not be ensured completely. In addition, the lack of standardization and automation is highly limiting for the patient safety and for a user-friendly application of the system.

A device as well as a method for the citrate anti-coagulated extracorporeal blood purification can be found in US 2007/066928 A1. The document discloses a means for detecting an ion concentration, which, among others, measures bivalent cations, such as calcium and magnesium ions, and which is arranged downstream from the dialysis unit in the extracorporeal blood circuit. The metering of citrate-containing solutions, which can be infused into the extracorporeal blood circuit upstream of and downstream from the dialysis unit, is regulated as a function of the measured ion concentration. The metering of the calcium and magnesium-containing electrolyte solution takes place independent on the measured ion concentration. First and foremost, the disadvantage of the device or of the method shown in US 2007/066928, respectively, is that it is not possible to draw a conclusion to the intracorporeal physiological state of the patient. Complications, such as hypocalcaemia due to an incorrect metering of the citrate or the electrolyte solution, respectively, cannot be recognized in due time. The patient safety can thus not be completely ensured.

A further device as well as a method for the citrate anti-coagulated blood purification is shown in US 2004/133145A1. The infusion rates for the citrate and for the substitution medium are adjusted as a function of measured flow rates. In the case of this device or this method, respectively, the patient safety can also not be completely ensured.

US 2007/0007184 A1 discloses an extracorporeal blood purification system, however without citrate anti-coagulation system. The blood purification system encompasses a disposable sensor, by means of which calcium can also be measured, among others. A further device as well as method for the extracorporeal blood purification without citrate anti-coagulation is disclosed in EP 1 175 917.

DE 101 14 283 C2 discloses a method for detecting the ion concentration of the blood of a patient in the case of the citrate anti-coagulated hemodialysis and/or hemofiltration of the afore-mentioned type. Preferably, the ions are calcium and/or magnesium ions, wherein calcium ions are preferably determined.

FIG. 1 shows a device, which is suitable for these purposes and which has also become known from DE 101 14 283 C2. The device encompasses a hemodialyzer and/or hemofilter 101 as well as an extracorporeal blood circuit 102, which includes an arterial inflow 103 (arterial branch) from the patient to the hemodialyzer and/or hemofilter 101 and a venous discharge 104 (venous branch) from the hemodialyzer and/or hemofilter 101 to the patient. A citrate supply device 105 is located in the inflow 103 and a substitution medium supply device 106 is located in the discharge 104. The device furthermore has a dialysate line 107, which in turn encompasses a dialysate inflow 108 and a dialysate discharge 109. In this method, the ion concentration of the blood is determined indirectly by means of the ion concentration in the dialysate discharge 109. For this purpose, at least one means for detecting an ion concentration 110, which can be an ion-sensitive sensor, e.g., is located in the dialysate discharge 109. This means for detecting an ion concentration 110 is connected to a regulating unit as well as to the supply devices for citrate and/or for the substitution medium. To be able to determine the ion concentration of the blood by means of the method described in DE 101 14 283 C2, the ions in the dialysate must be present in non-complexated form. One possibility is a temporary interruption of the citrate infusion into the blood circuit. The other possibility is the release of the ion from the ion-citrate complex, for example by changing the pH-value by infusing acid 111 into the dialysate discharge 109 upstream of the means for detecting an ion concentration 110.

The large advantage of the method of DE 101 14 283 C2 is that access into the blood-sided portion of the extracorporeal tube system is not necessary for detecting the ion concentration of the blood. This faces the following disadvantages. As already mentioned above, a determination of the ion concentration of the patient blood, which is very close-meshed and advantageously continuous as well as as accurate as possible, is necessary for a progress of the citrate anti-coagulation, which ensures the safety. A brief interruption of the citrate addition for determining the ion concentration of the blood according to the one approach described in DE 101 14 283 C2 accordingly provides only for a discontinuous monitoring of the ion concentration and consequently for a discontinuous control of the anti-coagulation. Even in response to a brief interruption of the citrate supply, it cannot be ensured completely that a sufficient anti-coagulation can be ensured.

In the event that the ion concentration of the blood is detected via the ion concentration of the dialysate by releasing the ion from the ion-citrate complex according to the other approach in DE 101 14 283 C2, an interruption of the citrate supply is not necessary. Highly limiting for this embodiment is the relatively large effort and, above all, the difficulty of more accurately determining the ion concentration of the blood, because this is utterly impossible due to the low clearance of the ion-citrate complex as compared to free ions and a possibly incomplete release of the complexated ions. An inaccurate determination of the ion concentration thus holds the large risk of an incorrect metering of the infusion solution. To determine the ion concentration of the blood by means of the concentration in the dialysate, the blood and dialysate flow must be included according to the method disclosed in DE 101 14 283 C2, because the dialysate flow during the treatment is typically greater than the blood flow and the ion concentration of the blood thus does not correspond to the ion concentration of the dialysate. The determination of the ion concentration of the blood can either be carried out mathematically, which, however, does not allow for an accurate determination, or advantageously—because only then is it possible to make a more accurate determination—by means of reducing the dialysate flow and an accompanying adaptation of the ion concentration of the dialysate to the ion concentration of the blood. A decrease of the dialysate flow, however, involves the disadvantage that the dialysis effectiveness during this time is lowered. In the case of certain patient groups, e.g. patients having liver diseases, there is a risk of an intracorporeal citrate accumulation when the dialysate flow and thus also the effective citrate clearance are reduced in response to continuous citrate infusion. A decrease of the dialysate flow furthermore extends the duration of the dialysis for the patient and, from an economical point of view, leads to an increased use of resources. An accurate and simultaneously very close-meshed or advantageously continuous determination of the ion concentration of the blood can thus not be carried out with the method in DE 101 14 283 C2 in response to a continuously running dialysis. In addition, an automation and standardization of the citrate anti-coagulation is difficult due to the complexity of the system.

In summary, the current problems of the citrate anti-coagulation cannot be solved to a satisfactory degree with the above-cited state of the art in response to the clinical application.

SUMMARY OF THE INVENTION

The invention came about in the context of a research project in cooperation with the Center for Biomedical Technology at the Donau University Krems. The goal of the project is the development of an automated online citrate-calcium anti-coagulation system for a simple and safe application. "Online" refers to a continuous regulation of the calcium level of the patient by means of a sensor and an adaptation of the citrate and calcium infusion rates. The calcium infusion is thereby regulated by means of a calcium sensor. A special device—a "citrate-calcium monitor", which substantially includes two infusion pumps, was developed for this. The citrate and calcium infusion can be controlled specifically by means of the "citrate-calcium monitor". A special algorithm computes the calcium infusion rate as a function of the blood flow rate and of the measured ionized calcium in the patient. A description of a "citrate-calcium monitor" without calcium sensor is described in [Schrefl A, Kellner K H, Hartmann J, Strobl W, Falkenhagen D (2001), A novel monitor for Anticoagulation with citrate. Int. J. Artif. Organs 24/8, 15].

The object of the invention presented herein is the improvement of the detection of the ion concentration of the blood when carrying out and monitoring the local citrate anti-coagulated extracorporeal blood purification. The main focus is thereby the patient safety. To ensure this, a reliable determination and careful monitoring of specific blood parameters—mainly the calcium ion concentration of the blood—and a strict and automated regulation of the supply rates of the citrate and of the substitution medium, which are made possible through this, are of highest importance.

This object is solved by means of a device of the aforementioned type, in the case of which, according to the invention, the ion concentration measuring means is adapted for the continuous generation of measuring values and is arranged upstream of the citrate supply point and the controller is adapted to continuously carry out a regulation of the metering of the citrate and of the substitution medium in consideration of a target value or target value range, which can be predetermined downstream from the citrate supply point.

This object is further fulfilled by means of a method of the afore-mentioned type, in the case of which, according to the invention, the ion concentration is continuously measured in a blood inflow of the extracorporeal blood circuit between patient and dialysis unit at least at a point upstream of the citrate supply point, wherein the control of the metering of the citrate and of the substitution medium is continuously carried out in consideration of a target value or target value range, which can be predetermined downstream from the citrate supply point.

Thanks to the invention, the problems, which are specific to the state of the art, can be solved in a simple manner. The invention involves particularly large advantages with reference to the patient safety. Due to the continuous measuring value detection, the metering of the substitution medium can be adjusted in very small time intervals. The metering of the citrate and of the substitution medium takes place in consideration of a target value or target value range, which can be predetermined downstream from the citrate supply point. The target value or target value range can be predetermined in the controller and can be adjusted by means of the user. The target value or target value range can be changed or newly adjusted at any time during the blood purification, if necessary. The invention thus makes it possible to continuously carry out and monitor the anti-coagulation and the substitution. The Ca- and Mg-ions are available in a still non-complexated form upstream of the addition point for citrate and can be determined quantitatively—and of course also qualitatively—without requiring an inhibition of the ion-citrate complex, as is the case in the above-cited state of the art. The continuously determined measuring value at this position in the blood circuit represents the continuously determined "current ion concentration of the blood", thus the one prior to the anti-coagulation and the blood purification, and consequently represents the current intracorporeal physiological state of the patient at the time of the measuring. The substitution medium is metered as a function of a comparison between a setpoint value range and the measured ion concentration. A setpoint value can also be adjusted instead of a setpoint value range.

Due to the continuous monitoring of the ion concentration—preferably of the Ca-ion concentration—of the blood at this position, the system can react at an early stage and very rapidly to a trend towards an undesired physiological state. The development of hypocalcaemia in the patient can thus be recognized at a very early stage. A hypocalcemia can occur very rapidly in certain patient groups and can already represent a life-threatening complication within a short time. Contrary to the state of the art, the measuring of the ion concentration of the blood in the blood-sided portion of the extracorporeal circuit further not only provides for a very close-meshed or continuous quantification of the ions, but simultaneously—as a function of the used sensor—also a very accurate one. A further large advantage of this method with reference to patient safety results from the fact that a continuous and accurate measuring value determination contrary to the state of the art can be carried out substantially without an impact on the regional anti-coagulation and/or dialysis effectiveness, which is contingent on measuring technologies. Due to the complexity of the control of the method according to the invention, which is low as compared to the above-cited state of the art, the citrate anti-coagulation can be carried out in a user-friendly and automated manner.

BRIEF DESCRIPTION OF THE DRAWINGS

The invention including further advantages will be defined in more detail below by means of the enclosed drawings and non-limiting exemplary embodiments.

FIGS. 6a-e show exemplary embodiments for sensors.

DETAILED DESCRIPTION OF THE INVENTION

Figure 1:
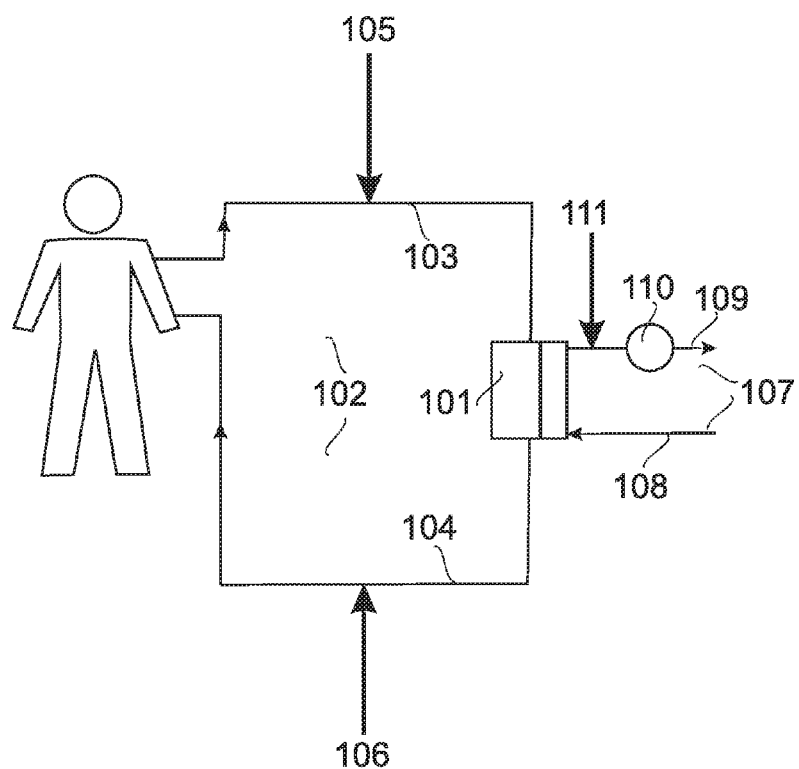
FIG. 1 shows a schematic illustration of a citrate anti-coagulated blood purification, as it is known from DE 101 14 283 C2.

The basic idea of the invention is a measuring of the ion concentration of the blood, which is carried out continuously, and an accompanying regulation of the citrate anti-coagulation, which is continuously carried out and which can be carried out in an automated manner, thanks to the invention. The ion concentration of the blood is thereby not indirectly determined by means of the ion concentration in the dialysate, as is the case in the above-cited state of the art, but directly on the blood side in the extracorporeal blood circuit.

According to the invention, the term "continuously" refers to a measuring of the ion concentration of the blood in regular time intervals, wherein the time intervals are advantageously kept brief, so as to monitor the ion concentration in a sufficiently close-meshed manner. Sufficiently brief time intervals are such, in the case of which it can be ensured that a development towards an unphysiological state of the patient can be identified in due time and that this development can be counteracted.

The further developments of the method according to the invention correspond to the further developments of the device according to the invention.

Due to the already mentioned importance of the calcium and magnesium ions in physiological processes in the human body, it is advantageous when the ion concentration measuring means measures alkaline earth ions.

In view of the significance of the calcium in response to the anti-coagulation, it is advantageous for the practical application of the invention when the ion concentration measuring means measures calcium ions.

It is further advantageous for the invention when the ion concentration measuring means is an ion-sensitive sensor.

To keep the effort as well as the costs for the measuring low, it is particularly applicable when the ion concentration measuring means is an optical ion-sensitive sensor.

In response to the practical performance, an embodiment in the case of which the ion concentration measuring means is an optical ion-sensitive sensor based on fluorescence has proven to be advantageous.

In an advantageous embodiment, provision can be made for the ion concentration measuring means to be introduced into the extracorporeal blood circuit. In the case of this embodiment, the measuring takes place in the blood-sided portion of the extracorporeal circuit and the ion concentration measuring means—preferably an ion-sensitive sensor—is in contact with the blood, which flows past. This leads to high demands on the characteristic of the sensor, because it must satisfy the demands for sterility, biocompatibility and cost efficiency. In terms of the invention, the term "biocompatibility" refers to a biological compatibility between a material—according to the invention the sensor surface—and a biosystem—according to the invention the blood. At the same time, it is necessary for accurate and reliable concentration values to be detected continuously by means of the sensor. The accuracy of the obtained measuring values depends on the used sensor. Sensors, which fulfill the above-mentioned requirements, are already known from the state of the art and are described in WO 2006/029293 and in U.S. Pat. No. 4,344,438, for example. The sensor device described in WO 2006/029293 is provided in particular for extracorporeal blood circuits, among others. Methods and sensor devices, which are introduced into the blood flow and which detect the concentration of specific elements by means of their optical characteristics, are also particularly advantageous. A description for such a method and a sensor device is found in U.S. Pat. No. 4,344,438, for example.

According to a further advantageous embodiment, provision can be made for a small quantity of blood to be branched off from the extracorporeal blood circuit via at least one bypass line and for at least one ion concentration measuring means to be arranged in this bypass line. In the case of this embodiment, the demands with reference to the biocompatibility are not limiting, because the small quantity of branched-off blood is no longer returned into the extracorporeal blood circuit after the measuring, but is discarded.

In view of patient safety, the device according to the invention can furthermore advantageously be provided with additional ion concentration measuring means:

For instance, provision can be made for an additional ion concentration measuring means to be arranged downstream from of the citrate supply point and upstream of the dialysis unit. According to the invention, an additional measuring of the ion concentration thereby takes place downstream from the citrate supply point and upstream of the dialysis unit, wherein the measured ion concentration is a control variable for the citrate supply rate and is compared to a setpoint value and/or setpoint value range as actual value and an exceeding of the setpoint value and/or setpoint value range causes an increase of the citrate supply rate and an undershooting of the setpoint value and/or setpoint value range causes a decrease of the citrate supply rate.

In a further alternative, provision can be made for an additional ion concentration measuring means to be arranged downstream from the dialysis unit and upstream of the substitution medium supply point. An additional measuring of the ion concentration can thus be carried out downstream from the dialysis unit and upstream of the substitution medium supply point, wherein the measured ion concentration is a control variable for the substitution medium supply rate.

According to a further alternative, provision can be made for an additional ion concentration measuring means to be provided downstream from the substitution medium supply point. In this alternative, an additional measuring of the ion concentration takes place downstream from the substitution medium supply point, wherein the measured ion concentration is a control variable for the substitution medium supply rate and is compared to a setpoint value range as actual value, wherein an exceeding of the setpoint value range causes a decrease of the substitution medium supply rate and an undershooting of the setpoint value range causes an increase of the substitution medium supply rate.

In the context of the invention, it is further possible for an additional ion concentration measuring means to be arranged in a plasma circuit. In this alternative, the ion concentration can additionally be measured in the plasma circuit, wherein the measured ion concentration is a control variable for the citrate supply rate and is compared to a setpoint value and/or setpoint value range as actual value and an exceeding of the setpoint value and/or setpoint value range causes an increase of the citrate supply rate and an undershooting of the setpoint value and/or setpoint value range causes a decrease of the citrate supply rate. This is only advantageous when the plasma circuit is closed, because only then does the ion concentration in the plasma circuit adjust in such a manner that reliable measuring values can be obtained.

In the event that one of the ion concentration measuring means supplies a measuring value outside of a predefinable setpoint value and/or target value range, an alarm can be triggered and the supply of the citrate and of the substitution medium can be stopped. Any alarm from the metering devices can lead to an alerting of the blood purification system and guides it into a safe state. This alarm can take place in the form of an acoustic and/or optical signal, for example.

To be able to carry out the citrate anti-coagulation in an automated manner and to keep the patient safety high, it is advantageous for the metering devices for citrate and for the substitution medium and the extracorporeal blood purification system to be connected to one another via the controller by means of signal connections, wherein the controller is adapted to include signals from the extracorporeal blood purification system supplied to it into its regulation. Signals from the extracorporeal blood circuit can be a change of the level of the extracorporeal blood flow or of the dialysate flow, the type of the used dialyzer/hemofilter, the adjusted ultrafiltration rate, a stopping of the blood pump or an alarm, which causes the standstill of the extracorporeal blood flow, for example. The level of the extracorporeal blood flow [ml/min] is the blood volume, which is pumped by the blood pump per time unit.

It is further advantageous when the metering devices for citrate and for the substitution medium and the extracorporeal blood purification system are connected to one another via the controller by means of signal connections, wherein the controller is adapted to include signals from the extracorporeal blood purification system supplied to it into its regulation.

Such signals from the metering devices can be a used up citrate solution or a used up substitution medium, respectively, a pinched tube or the presence of air bubbles in the tube, for example.

In the case of a filtration device of the extracorporeal blood purification system, wherein the metering devices for citrate and for the substitution medium and the extracorporeal blood purification system are connected to one another via the controller by means of signal connections, it is furthermore advantageous when the controller is adapted to initiate a proportional change of the ultrafiltration quantity of the filtration device in response to a change of the citrate supply rate and/or of the substitution medium supply rate or to propose this to an operator. As already mentioned, provision can be made in the course of the dialysis treatment for liquid to be drawn from the patient (ultrafiltration). The contribution of the ultrafiltration to the blood purification is insignificant and only serves for the removal of liquid build-up in the patient. In the event that the used citrate solution or the substitution medium solution, respectively, is concentrated so as to be very low, a larger liquid volume, which must be removed again by means of ultrafiltration, reaches into the extracorporeal blood circuit in the course of the supply of the citrate or of the substitution medium, respectively, and thus to the patient. Moreover, the hematocrit may change in response to the ultrafiltration. As will be defined below in more detail, the hematocrit is an important parameter which should be considered in response to the supply of the citrate and/or of the substitution medium.

To keep patient safety as high as possible, it is advantageous when the ion concentration is continuously measured in regular time intervals. The time intervals should be as brief as possible, so that the monitoring and control of the citrate anti-coagulation takes place as close-meshed as possible. A time interval of 30-60 minutes is sufficient in the case of most applications.

In the case of certain patient groups, such as patients having liver diseases or persons having low body weight (mainly children), e.g., it is advisable when the time interval between two subsequent measurings is maximally 10 minutes.

To provide for the most close-meshed or continuous detection of the ion concentration as possible, it is advantageous when a measuring signal is generated by means of a single ion concentration measuring means in regular time intervals. Corresponding to the ion concentration measuring means or the sensor system, the sensor can operate either with or without interruption. The sensor can be recalibrated during the interruption.

A close-meshed measuring value detection is also made possible by means of an alternative, in the case of which the ion concentration is measured alternately or periodically, respectively, by two or a plurality of essentially similar ion concentration measuring means, wherein a measuring signal is generated in regular time intervals. In the case of this alternative, the measurings can be carried out in a very close-meshed manner, because a recalibration of the respective ion concentration means, which does not currently measure, is possible by means of a brief rinsing with a calibration solution, for example.

In addition to the quantification of the ions, it is reasonable for the person of skill in the art that provision can also be made in the context of the invention for the ions to not only be capable of being determined quantitatively, but also qualitatively. It goes without saying that instead of sensors it is also possible to use other methods to determine the ion concentration, for example a measuring by means of ionometers.

To adjust the metering of the citrate supply and to regulate the citrate supply rate, it is advantageous for the invention when the initial calcium ion concentration and the hematocrit are considered as parameters in response to the metering of the citrate and of the substitution solution and when the level of the extracorporeal blood flow is a control variable for the citrate supply rate, wherein a change of the level of the extracorporeal blood flow causes a proportional change of the citrate supply rate. The citrate supply rate is the quantity of citrate, which is introduced into the extracorporeal blood circuit at a citrate supply point per time unit. The citrate supply rate is thereby adjusted and is regulated during the course of the treatment in such a manner that an effective anti-coagulation is ensured. According to the invention, different parameters are considered to adjust the citrate supply rate:

The initial calcium ion concentration of the patient is the calcium ion concentration, which is detected once prior to the onset of the blood purification. Based on this value, the citrate supply rate is adjusted at the onset of the treatment.

To adapt the administered citrate dose to the individual needs of the patient, the hematocrit is further considered to be a parameter in response to the adjustment of the required citrate dose. The quantity of citrate, which is required for an effective anti-coagulation, is influenced by the hematocrit. The reason for this is the fact that citrate cannot permeate the cell membranes of the blood cells and thus only disperses in the plasma. In the case of patients with low hematocrit, a higher citrate dose is thus necessary for an effective anti-coagulation and vice versa. The hematocrit is determined once prior to the onset of the treatment, thus represents the initial hematocrit and is considered as a constant factor for the citrate supply rate. It goes without saying that a person of skill in the art in the field will recognize that it is possible in terms of the invention to not only determine the hematocrit initially, but again during the entire dialysis process in time intervals and to accordingly adapt the addition of citrate to the hematocrit values.

To keep the metering of the citrate and thus the local anti-coagulation as accurate as possible, it is further advantageous when the level of the extracorporeal blood flow is a control variable for the citrate supply rate, wherein a change of the level of the extracorporeal blood flow causes a proportional change of the citrate supply rate. The citrate supply rate is coupled to the extracorporeal blood flow via a constant factor, so that a change of the extracorporeal blood flow causes a change of the citrate supply rate. In the case of an increase of the blood flow, the citrate supply rate is also increased. In the event that the blood flow is stopped, for example triggered by means of a breakdown of the blood pump, the citrate supply thus stops as well.

The metering of the citrate can be adjusted in a highly accurate manner when the bond of the calcium ions to proteins in the blood is furthermore considered as a parameter in response to the metering of the citrate. The bond of the calcium ions to citrate is influenced by means of the proteins in the blood, in particular albumin, thus leading to the formation of protein-calcium complexes. The law of mass action can be used to compute how many calcium ions are present in a protein-bound manner. The citrate supply rate is adjusted at the onset of the treatment in consideration of this parameter.

By adding the citrate, the calcium ion concentration is lowered to a desired target value and/or target value range. It is thus advantageous for the method according to the invention when the target value and/or target value range, which can be predetermined downstream from the citrate supply point, represents the calcium ion concentration of the anti-coagulated blood, which is present between the citrate supply point and the dialysis unit. It is sensible for the target value and/or target value range to be the calcium ion concentration, in the case of which a blood clotting in the filter is effectively prevented. Target values, which specify values in the range of from 0.25 to 0.35 mmol/l [Kutsogiannis et al. (2000), Am J Kidney Dis, Vol. 35:802-811; Tolwani et al. (2001), Kidney International, Vol. 60:370-374] or <0.4 mmol/l [Swartz et al. (2004), Clinical Nephrology, Vol. 61(2):134-143] as threshold values for the calcium ion concentration in the anti-coagulated blood, can thereby be found in the literature. The calcium ion concentration should be regulated within these ranges.

It is thus particularly advisable for the patient safety when the calcium ion concentration of the anti-coagulated blood can be chosen in a range between 0.15-0.5 mmol/l and in particular between 0.2-0.4 mmol/l. The target value can be chosen individually, corresponding to the state and the needs of the patient. For instance, it can be necessary for some patients to adjust the target value to 0.15 mmol/l, while a higher target value of up to 0.5 mmol/l is optimal for other patients. Ideally, a value of approx. 0.2 mmol/l is to be aimed for, because the complement activation is also highly reduced in response to this value. This target value and/or target value range is predetermined at the onset of the treatment and can be adjusted by the user. The target value and/or target value range can be changed and newly adjusted during the blood purification, if necessary.

In the event that the ion concentration measured upstream of the citrate supply point exceeds or undershoots a previously defined setpoint value range, provision can thus be made for the ion concentration measured upstream of the citrate supply point to be a control variable for the citrate supply rate, wherein the measured ion concentration as actual value is compared to a setpoint value range and an exceeding of the setpoint value range causes an increase of the citrate supply rate and an undershooting of the setpoint value range causes a decrease of the citrate supply rate. As already mentioned, the ion concentration measured upstream of the citrate supply point—preferably the calcium ion concentration—represents the current intracorporeal physiological state of the patient. The setpoint value range thus comprises ion concentration values, which correspond to a physiological state. It goes without saying that undershooting or exceeding of the setpoint value range can also trigger an alarm.

To optimally adjust the metering of the substitution medium to maintain the physiological state of the patient, it is advantageous for the practical application when the ion concentration measured upstream of the citrate supply point is a control variable for the substitution medium supply rate, wherein the measured ion concentration as actual value is compared to a setpoint value range and an exceeding of the setpoint value range causes a decrease of the substitution medium supply rate and an undershooting of the setpoint value range causes an increase of the substitution medium supply rate.

The citrate clearance and/or the calcium ion clearance of the dialysis unit can further be a control variable for the substitution medium supply rate, wherein an increase of the citrate clearance or a decrease of the calcium ion clearance, respectively, causes a decrease of the substitution medium supply rate and a decrease of the citrate clearance or an increase of the calcium ion clearance, respectively, causes an increase of the substitution medium supply rate. The extent of the removal of the citrate, of the ion-citrate complex or of the calcium ions, respectively, by means of the dialysis filter (citrate clearance or calcium ion clearance, respectively), is a function of the used filter as well as of blood and dialysate flow or the ratio of blood to dialysate flow, respectively. It is thus advisable when the citrate clearance and/or the calcium ion clearance of the dialysis unit are considered in response to the substitution of the Ca- and possibly of the Mg-ions. The substitution medium, which is introduced into the extracorporeal circuit downstream from the dialysis filter typically includes mainly Ca-ions (or additionally also Mg-ions, respectively).

The citrate clearance and/or calcium ion clearance, which is to be expected, can be communicated to the citrate anti-coagulation system, in that the used filter is input into the system by the user prior to the onset of the treatment. In the alternative, the clearance can be communicated by inputting the filter type (high flux/low flux) and the effective membrane surface. It is important for the determination of the citrate clearance or of the calcium-ion clearance, respectively, to communicate the blood and the dialysis flow to the citrate monitor.

It is further highly relevant for patient safety when the citrate supply rate is considered in response to the regulation of the substitution medium supply rate, wherein an increase of the citrate supply rate causes an increase of the substitution medium supply rate and a decrease of the citrate supply rate causes a decrease of the substitution medium supply rate. In the event that the citrate supply is interrupted, for example by means of a pump breakdown, the supply of the substitution medium is also interrupted.

Exemplary Embodiments

The citrate anti-coagulated blood purification method according to DE 101 14 283 schematically illustrated in FIG. 1 was already explained in detail above in the description of the state of the art.

Figure 2:
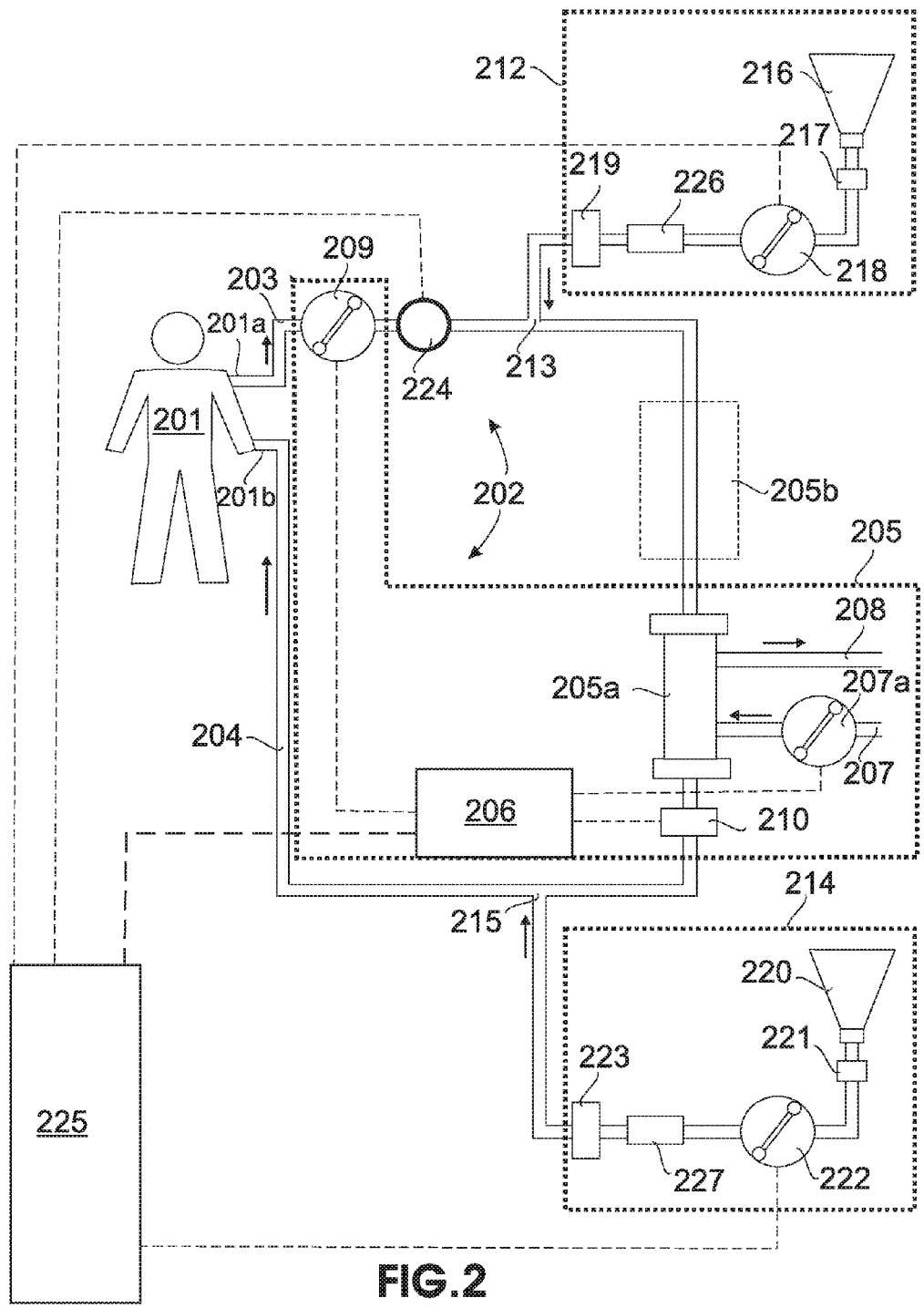
FIG. 2 shows a schematic illustration of a first preferred embodiment of an automated citrate anti-coagulated blood purification according to the invention.
Figure 4:
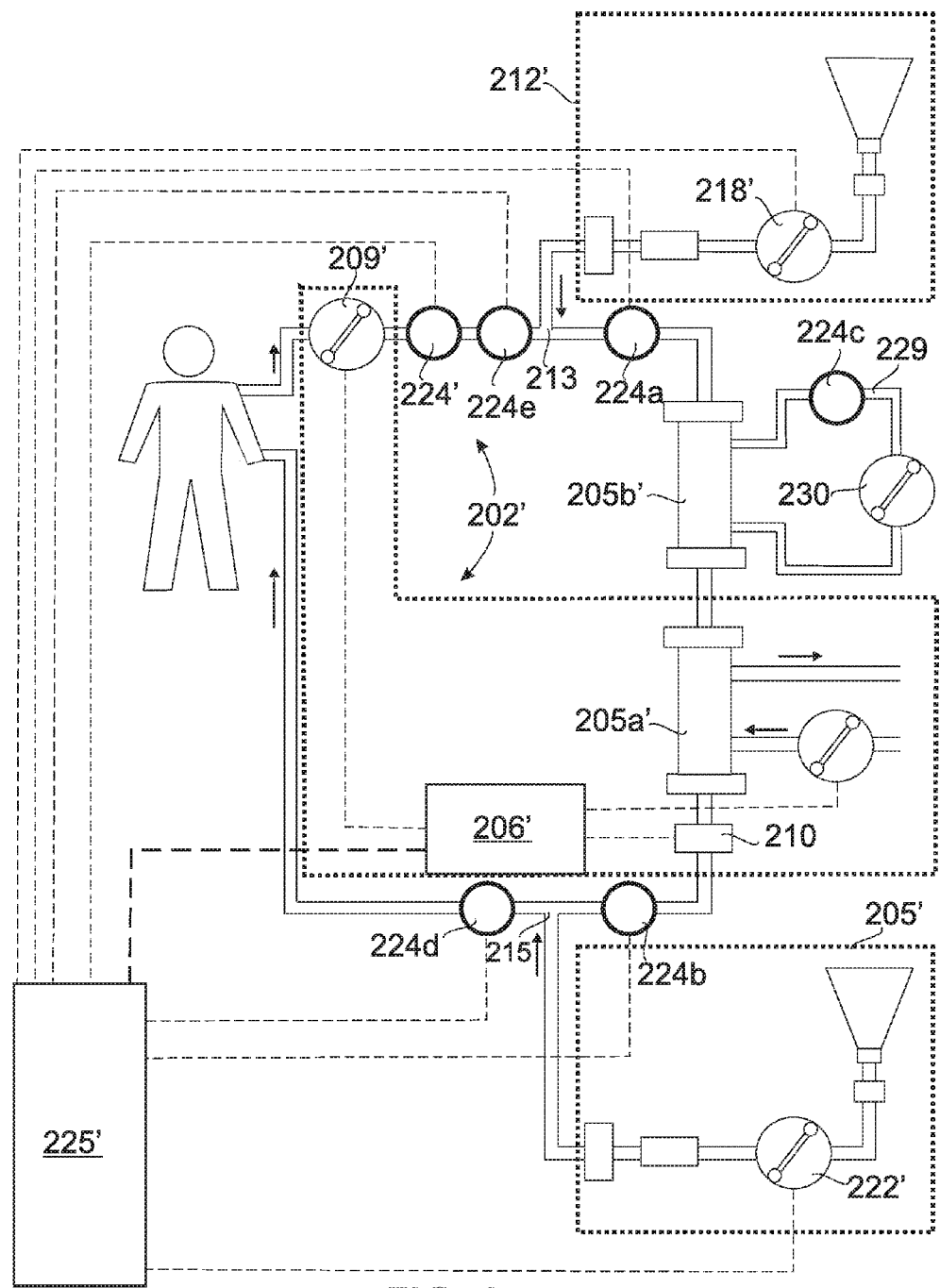
FIG. 4 shows a schematic illustration of a second, upgraded embodiment
Figure 5:
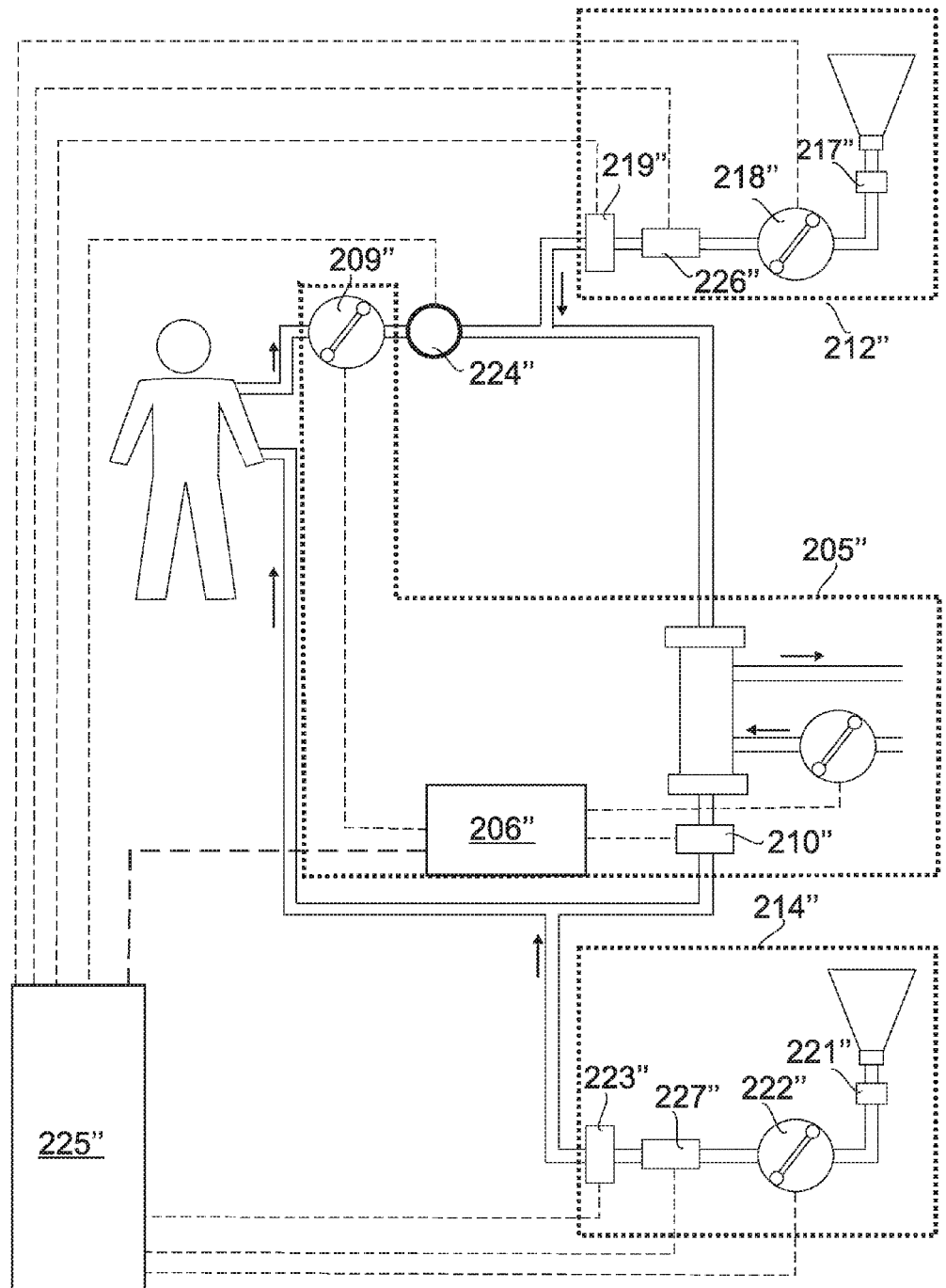
FIG. 5 shows a schematic illustration of a third embodiment, which triggers an alarm in response to malfunctions.

The signal connections of the individual device components to one another or to the controllers, respectively, are symbolized in FIGS. 2, 4 and 5 by means of dashed lines.

FIG. 2 shows a schematic illustration of a preferred embodiment of an automated citrate anti-coagulated blood purification method according to the invention. Via an arterial access 201a, the blood of the patient 201 reaches into the extracorporeal blood circuit 202 comprising a blood inflow 203 (arterial branch), a blood discharge 204 (venous branch) and a dialysis unit 205 located therebetween (illustrated by means of a dashed border) and flows back into the patient again via a venous access 201b. The dialysis unit 205 is substantially comprised of a dialysis filter 205a, a blood pump 209, an air trapping comprising an air bubble detector 210 and a controller 206. Depending on the blood purification system and required treatment, provision can be made upstream of the dialysis filter 205a for an additional blood purification element 205b—for example a hemofilter, a hemofilter comprising a closed plasma circuit or an adsorber circuit. In the dialysis filter 205a, the blood is connected to the dialyzing liquid via a semi-permeable membrane. The dialyzing liquid is typically produced by the dialysis device and is pumped via a dialysate inflow 207 into the dialysis filter 205a by means of a dialysate pump 207a and is discharged and disposed of via a dialysate discharge 208 after passing through the dialysis filter 205a. Coming from the patient, the blood is pumped through the extracorporeal blood circuit 202 by means of the blood pump 209, wherein the level of the blood flow $Q_B$ is adjusted via the blood pump 209. As will be described below, the blood flow $Q_B$ [ml/min] is an important parameter for the system and represents the blood volume, which is pumped by the pump per time unit. Typically, a blood flow $Q_B$=50-400 ml/min is adjusted in the case of the hemodialysis.

Before the blood reaches back into the patient 201, it passes through an air trapping comprising an air bubble detector 210 for the purpose of avoiding an air embolism. The above-described components 202-210 form a typical embodiment of an extracorporeal blood purification system.

FIG. 2 further shows a device for the citrate anti-coagulation by means of a controlled citrate metering device 212 for supplying citrate at a citrate supply point 213 upstream of the dialysis filter 205a (and of the blood purification element 205b, if available) and a controlled substitution medium metering device 214 for supplying a substitution medium at a substitution medium supply point 215 downstream from the dialysis filter 205a. The citrate metering device 212 encompasses a container comprising citrate solution 216, a drop detector 217, a citrate pump 218, a pressure sensor 226 and an air bubble detector 219. The blood is stopped from clogging by means of the infusion of the citrate solution, either in the form of $Na_3$ citrate or ACD-A (acid citrate dextrose-A), which in addition to citrate also includes citric acid and dextrose, at the citrate supply point 213 into the extracorporeal blood circuit 202. A low concentration of the citrate solution, as is the case with an ACD-A solution, for example, leads to a relatively large liquid volume, which reaches into the extracorporeal blood circuit 202 per time unit. For this reason, it is necessary to consider this in the case of the ultrafiltration quantity of the dialysis device. Similar to the citrate metering device 212, the substitution medium metering device 214 also includes a container comprising substitution medium 220, a drop detector 221, a substitution medium pump 222, a pressure sensor 227 and an air bubble detector 223. The substitution medium mainly includes Ca-ions or Ca- and Mg-ions and is infused into the extracorporeal blood circuit 202 at the substitution medium supply point 215. A supply of the substitution medium via a separate venous access would also be possible, but is not desired for safety reasons.

The pump speed of the pumps 218, 222 is determined and monitored by means of hall sensors and incremental sensors, which are integrated into the pump 218, 222.

The measuring of the patient ion concentration takes place by means of an ion concentration measuring means arranged upstream of the citrate supply point 213, which, in the embodiment shown in FIG. 2, is a Ca-ion sensor 224 by means of which the Ca-ion concentration is measured sensitively and specifically. It is not important thereby whether the Ca-ion sensor 224 is arranged downstream from or upstream of the blood pump 209. For the measuring, a small quantity of blood can be branched off from the extracorporeal blood circuit 202 in regular time intervals in the case of an alternative and can be supplied to the Ca-ion sensor 224, wherein the blood is discarded after the measuring. It goes without saying that it is also possible to integrate a biocompatible Ca-ion sensor 224 directly into the extracorporeal blood circuit. The sensor device known from WO 2006/029293 could be combined with a biocompatible Ca-ion-sensitive sensor surface, for example.

The measurings are carried out in regular time intervals, wherein the time interval is chosen in such a manner that a trend towards an unphysiological state of the patient is recognized in due time. In the case of most of the applications, a time interval of 30-60 minutes is sufficient. In the case of certain patient groups, e.g. patients having liver diseases, the time interval between two subsequent measurings is maximally 10 minutes.

The two metering devices 213, 214 and the Ca-ion sensor 224 are connected to a controller 225. The controller 225 is further connected to the controller 206 of the dialysis unit 205. To carry out the citrate anti-coagulated blood purification method in an automated manner, provision is made for the controller 225, by means of which the Ca-ion sensor 224, the two metering devices 213, 214 and the control of the dialysis unit (e.g. a Fresenius 4008/5008 dialysis machine) are connected to one another via a control algorithm. The controller 225 has the tasks of controlling and regulating the citrate and substitution medium pumps 218, 222, to evaluate the signals of the sensors 224, 226, 227 and detectors 217, 219, 221, 223, to trigger alarms in the case of malfunctions, to turn off the pumps 218, 222 in response to malfunction, to store data and to communicate with the blood purification device.

To meter the citrate and the substitution medium, the "citrate-calcium monitor", which was developed at the Donau University Krems (Center for Biomedical Technology) and which is cited in the state of the art, can be used.

A simple control loop is created to control the citrate anti-coagulation:

The citrate supply rate $Q_{cit}$ is adjusted in consideration of a target value, which can be predetermined in the controller 225, wherein the initial Ca-ion concentration of the blood and the initial patient hematocrit are considered in response to the adjustment of the citrate supply rate $C_{cit}$ and the level of the blood flow is a control variable for the citrate supply rate $C_{cit}$. The initial ion concentration of the blood is detected prior to the onset of the treatment, either by means of the Ca-ion sensor 224 or by means of a drawn blood sample. The initial hematocrit is also detected prior to the onset of the treatment by means of a blood sample. The target value and/or target value range represents the Ca-ion concentration of the anti-coagulated blood, which is present downstream from the citrate supply point 213 and upstream of the dialysis unit 205 and, practically speaking, it is the Ca-ion concentration, in the case of which a blood clotting in the filter is effectively prevented. Target values, which specify a Ca-ion concentration of 0.25 to 0.4 mmol/l, can thereby be found in the literature. Ideally, a value of approx. 0.2 mmol/l is to be aimed for, because the complement activation is also highly reduced in the case of this Ca-ion concentration. This target value and/or target value range can be predetermined at the onset of the treatment in the controller 225 and can be adjusted by the user. The target value and/or target value range can be changed and newly adjusted at any time during the blood purification.

Figure 3:
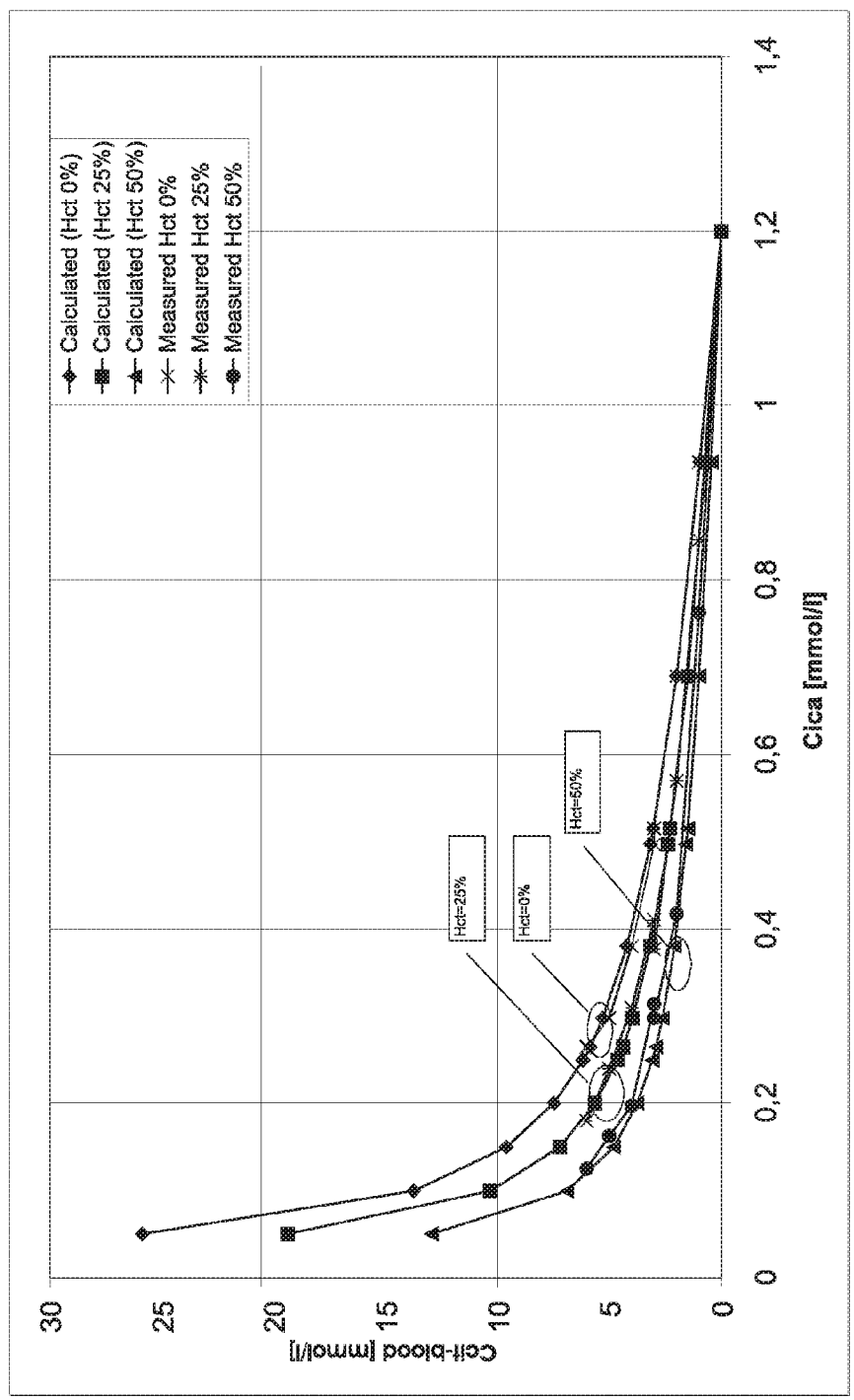
FIG. 3 shows a diagram, which shows the citrate concentration as a function of the free calcium ions and of the hematocrit and which is used to adjust the citrate supply rate.

The adjustment of the citrate supply rate $Q_{cit}$ is based on a mathematical model, which is shown by means of the diagram illustrated in FIG. 3.

The diagram shows the curve family of the Ca-ion lowering by means of citrate, wherein the citrate concentration in the blood $Q_{cit-blood}$ [mmol/l] is illustrated as a function of the target concentration of the free Ca-ions $C_{iCa}$ [mmol/l] in the anti-coagulated blood and of the initial hematocrit Hct [%]. The initial Ca-ion concentration of the blood lies at 1.2 mmol/l with very slight deviations. For the most part, the hematocrit values lie in a range between 25 and 50%. The characteristic curves were obtained either by measuring or by computation—based on hematocrit values of 0%, 25% and 50%.

The citrate concentration in the blood $C_{cit-blood}$ for lowering the Ca-ion concentration by means of complex formation is thereby computed from the following empirical formula:

1) Computation of the complex-bound calcium ions:

$$C_{complex-bound\ Ca} = 1.2\ mmol/l - C_{iCa}$$

2) 1 mmol calcium binds v mmol citrate in the complex:

$$C_{complex-bound\ citrate} = C_{complex-bound\ Ca} * v$$

3) From 1 and 2 follows:

$$C_{free\ citrate} = C_{cit-blood} - (1.2\ mmol/l - C_{iCa}) * v$$

4) From the law of mass action follows:

$$C_{free\ citrate} * C_{iCa} = p * C_{complex-bound\ Ca} =>$$
$$C_{free\ citrate} * C_{iCa} = p * (1.2\ mmol/l - C_{iCa}) => C_{free\ citrate} = p * (1.2\ mmol/l - C_{iCa}) / C_{iCa} => C_{cit-blood\ with\ Hct=0\%} = p * (1.2\ mmol/l - C_{iCa}) / C_{iCa} + v * (1.2\ mmol/l - C_{iCa})$$

$C_{iCa}$ target value of the concentration of free Ca-ions in the anti-coagulated blood
$C_{complex-bound\ Ca}$ concentration of complex-bound Ca-ions
$C_{cit\_blood}$ citrate concentration in the blood (total)
$C_{complex-bound\ citrate}$ concentration of complex-bound citrate
$C_{free\ citrate}$ concentration of the free citrate
p, v empirically found factors (p=1, v=2.5)

The adaptation of the citrate concentration in the blood to the patient hematocrit (Hct) takes place thereby by the application of the following formula:

$$C_{cit-blood\ with\ Hct[\%]} = C_{cit-blood\ with\ Hct=0\%} * (100\% - Hct[\%]) / 100\%$$

For a better overview, the characteristic curves associated to the respective hematocrit values (0%, 25%, 50%) are identified and labeled in the diagram. Needless to say, any characteristic curves $C_{cit-blood}$ can be computed from the afore-derived equations as a function of the iCa target concentration $C_{iCa}$ and the Hct.

Based on the desired target value and the initial hematocrit value, the necessary citrate supply rate $Q_{cit}$ is determined from the displayed array of curves in consideration of the level of the blood flow. This is illustrated by means of the following computation example:

The initial hematocrit Hct is 50% and the target value of the Ca-ion concentration after citrate addition is to be 0.2 mmol/l. According to the diagram in FIG. 3, the citrate concentration in the blood $C_{cit\ blood}$, which is necessary for an effective anti-coagulation is thus ~4.5 mmol/l. Assuming that the blood flow $Q_B$=250 ml/min and that the citrate concentration in the infusion solution $C_{cit}=500$ mmol/l, the citrate supply rate $Q_{cit}$ can be computed according to the law of mass action $Q_{cit}*Q_{cit}=Q_B*C_{cit\_blood}$.

$$Q_{cit}=(Q_B*C_{cit\_blood})/C_{cit}=(250 \text{ ml/min}*4.5 \text{ mmol/l})/500 \text{ mmol/l}=2.25 \text{ ml/min}=135 \text{ ml/h}$$

The citrate supply rate $Q_{cit}$ is adjusted prior to the onset of the treatment by adjusting the pump speed of the citrate pump 218—referring back to FIG. 2—and is adapted only to changes of the blood flow $Q_B$. In the event that the blood flow $Q_B$ does not change, the citrate supply rate $Q_{cit}$ remains the same during the entire treatment. To react to changes in the blood flow $Q_B$, the citrate supply rate $Q_{cit}$ is connected to the blood flow $Q_B$ via a constant factor. A stopping of the blood pump 209 and consequently of the blood flow is identified by the controller 206, is communicated by the controller 206 to the controller 225, which initiates a stopping of the citrate pump 218. In terms of the patient safety, it is thus prevented that citrate is still pumped into the extracorporeal blood circuit 202 in the event that the blood pump 209 is stopped. A change of the substitution medium supply rate is likewise initiated by the control unit 225 in response to a change of the citrate supply rate or the substitution medium pump 222 is stopped in response to the stopping of the blood pump 209 or of the citrate pump 218, respectively.

In the described embodiment, the citrate supply rate $Q_{cit}$ is not adjusted as a function of the Ca-ion concentration, which is measured by the Ca-ion sensor 224.

Needless to say, this does not preclude that the Ca-ion concentration, which according to the invention is measured by the Ca-ion sensor 224, can also be a control variable for the citrate supply rate.

The initial substitution medium supply rate $Q_{cit}$ is computed based on the citrate supply rate $Q_{cit}$ and the citrate clearance of the dialysis filter 205a and is regulated according to the previous rule as a function of the Ca-ion concentration measured by the Ca-ion sensor 224.

The substitution medium supply rate $Q_{Ca/Mg}$ is regulated by means of the substitution medium pump 222 as a function of the Ca-ion concentration of the blood measured by the Ca-ion sensor 224. The Ca-ion concentration measured by the Ca-ion sensor 224 thereby represents the actual value and is compared to a setpoint value range (e.g. 1.1-1.3 mmol/l).

In the event that the Ca-ion concentration of the blood lies in the range of from 1.1-1.3 mmol/l, the substitution medium supply rate $Q_{Ca/Mg}$ is kept.

In the event that the Ca-ion concentration lies below 1.1 mmol/l, the substitution medium supply rate $Q_{Ca/Mg}$ is increased by 10%.

In the event that the Ca-ion concentration lies above 1.3 mmol/l, the substitution medium supply rate $Q_{Ca/Mg}$ is lowered by 10%.

In the event that the Ca-ion concentration lies below 1.0 mmol/l or above 1.4 mmol/l, a warning is output and the operator is requested to consult a doctor.

The citrate pump 218 is connected via the controller 225 to the substitution medium pump 222 via a factor, which is computed according to the above rule. In the event that the blood flow is stopped, the citrate supply and consequently also the supply of the substitution medium are stopped automatically via the control algorithm. This control algorithm is very important for maintaining the patient safety and prevents an accumulation of citrate or Ca- and Mg-Ions, respectively, in the extracorporeal blood circuit 202 in response to the breakdown of the blood pump 209.

The Ca-ion concentration measured by the Ca-ion sensor 224 represents the current intracorporeal Ca-ion level and thus the physiological state of the patient. A trend towards an unphysiological state can thus be identified. For instance, an alarm can be triggered in addition to the regulation of the substitution medium supply rate $Q_{Ca/Mg}$ in response to an exceeding or undershooting of a threshold value range.

The citrate clearance is further considered in response to the substitution medium supply rate. The citrate clearance is a feature of the used dialysis filter and is a function of the blood and dialysate flow. Changes to the citrate clearance cause a change of the substitution medium supply rate. The operator thereby inputs the filter type into the controller 225 at the onset of the treatment. The blood pump 209 or the dialysate pump 207a, respectively, communicate changes in the citrate and dialysate flow to the controller 206 and these changes are communicated by said controller 206 to the controller 225, which in turn initiates an adaptation of the substitution medium supply by activating the substitution medium pump 222.

FIG. 4 shows a further embodiment of the invention comprising upgrades as compared to the embodiment illustrated in FIG. 2. The device shown in FIG. 4 corresponds to the one of FIG. 2, unless otherwise specified below. The illustrated upgrades can be used individually or in combination.

For instance, an additional means for detecting the ion concentration—a Ca-ion sensor 224a—can be arranged in the extracorporeal blood circuit 202' between the citrate supply point 213 and the dialysis unit 205'. The dialysis unit 205' is comprised of the blood pump 209', the dialysis filter 205a' and the controller 206'. The Ca-ion sensor 224a thus measures the Ca-ion concentration of the anti-coagulated blood prior to the entry into the dialysis unit 205'. In response to an effective anti-coagulation, the measuring value obtained at this position should have a value, which corresponds to the above-defined predeterminable target value and/or target value range.

An additional means for detecting the ion concentration—a Ca-ion sensor 224b—can furthermore be arranged between the dialysis unit 205' and the substitution medium supply point 215. To prevent interferences to the measuring caused by possibly existing air bubbles, it is better to arrange the Ca-ion sensor 224b downstream from the air trapping comprising the air bubble detector 210. The Ca-ion sensor 224b detects the Ca-ion concentration after the dialysis and thus provides for the accurate metering/control of the substitution medium.

For example, the additional blood purification element 205b is a hemofilter 205b' comprising a closed plasma circuit 229 and a filtrate pump 230. In plasma circuits, the plasma can be cleaned by means of an adsorber or by means of MDS (Microsphere Detoxification System), for example. In the event that the plasma circuit 229 is closed and the plasma is mixed well, an additional means for detecting the ion concentration—a Ca-ion sensor 224c—can be arranged in the plasma circuit 229. Due to the good mixture—the plasma frequently circulates through the plasma circuit 229—the Ca-ion concentration in the entire plasma circuit 229 is almost the same and the Ca-ion sensor 224c can consequently be positioned anywhere in the plasma circuit 229. In the case of blood purification systems comprising a plasma circuit 229, in the case of which a measuring of the Ca-ion concentration is provided between the citrate supply point 213 and the dialysis filter 205a', said measuring can take place by means of the Ca-ion sensor 224c in addition to or instead of a measuring by means of a Ca-ion sensor 224a.

The measuring values obtained by means of the Ca-ion sensors 224a and 224c are supplied to the controller 225' and have a regulating effect on the citrate supply rate $Q_{cit}$, in that the citrate pump 218' of the citrate metering device 212' is activated by the controller 225', wherein the obtained measuring values represent the actual values and are compared to a setpoint value and/or setpoint value range:

In the event that the Ca-ion concentration lies in a desired concentration range, in which an effective anti-coagulation and prevention of the complement activation is ensured (e.g. 0.2 mmol/l), the citrate supply rate $Q_{cit}$ is kept.

In the event that the Ca-ion concentration lies above the desired concentration range, in which an effective anti-coagulation is ensured (e.g. ≥0.2 mmol/l), the citrate supply rate $Q_{cit}$ of the current Ca-ion concentration is increased accordingly.

In the event that the Ca-ion concentration lies below the desired concentration range, the citrate supply rate $Q_{cit}$ of the current Ca-ion concentration is reduced accordingly.

The sensors 224a and 224c thereby measure the actual value and control the citrate supply, so that the actual value corresponds to the preadjusted target value. The controller 225' must check whether the citrate supply rate lies within a defined range so as to prevent an undesired overdose.

For safety reasons, a change of the citrate supply rate $Q_{cit}$ can initiate a change of the substitution medium supply rate $Q_{Ca/Mg}$, as already described above, in that the substitution medium pump 222' is activated by the controller 225'. An increase of the citrate supply rate $Q_{cit}$ causes an increase of the substitution medium supply rate $Q_{Ca/Mg}$ and a decrease of the citrate supply rate $Q_{cit}$ causes a decrease of the substitution medium supply rate $Q_{Ca/Mg}$.

According to a further upgrade illustrated in FIG. 4, an additional means for detecting the ion concentration—a Ca-ion sensor 224d—can be arranged downstream from the substitution medium supply point 215. The measuring values of the Ca-ion sensor 224d are used in a further embodiment of the citrate anti-coagulation for the metering/control of the substitution medium. At this position in the extracorporeal blood circuit 202', the blood is to again encompass physiological Ca- and Mg-ion values. The measuring values obtained by means of the Ca-ion sensor 224d are supplied to the controller 225' and a regulation of the substitution medium supply rate $Q_{Ca/Mg}$ is carried out according to the above-described Ca-ion sensor 224 (FIG. 2).

The arrangement of the sensors also provides for many possibilities for alternatives. A measuring of an ion concentration, which is as close-meshed as possible, upstream of the citrate supply point 213, which is the Ca-ion sensor 224 according to the embodiment in FIG. 2, is particularly important for the conversion of the invention. In response to the use of a Ca-ion sensor, which must be calibrated in regular intervals, a second essentially similar Ca-ion sensor 224e can be arranged upstream of the citrate supply point 213 (FIG. 4). The Ca-ion concentration is measured alternately by the two Ca-ion sensors 224', 224e, wherein one of the sensors is calibrated, while the other generates a measuring signal. The additional Ca-ion sensor 224e can also be adapted to control the function of the Ca-ion sensor 224' and to trigger an alarm in response to a malfunction, e.g. when the measuring values deviate too much from one another. The Ca-ion sensor 224e can operate either without or with interruptions. It goes without saying that the Ca-ion sensor 224e can also be sensitive for another ion type. For example, an alarm can be triggered due to a change of the ratio of the calcium and magnesium ions exceeding a threshold value, wherein the Ca-ion sensor 224' detects the Ca-ion concentration and the Ca-ion sensor 224e detects the Mg-ion concentration.

FIG. 5 shows a third embodiment, which can trigger an alarm in response to malfunctions. The device shown in FIG. 5 corresponds to the one of FIG. 2, unless otherwise specified below. To keep the safety for the patient as high as possible, provision is also made according to the invention for the individual modules—the citrate metering device 212", the substitution medium metering device 214" and the extracorporeal blood purification system (=the dialysis unit 205")—to be connected to one another such that an alarm, which is triggered by one of the metering devices 212", 214" or the dialysis unit 205", respectively, is recognized by the respective other modules and is reacted to accordingly. The communication between the individual modules takes place via the controllers 206", 225". The alarm is displayed optically and acoustically. An alarm can be triggered by means of the following malfunctions, for example.

The breakdown of one of the pumps 209", 218", 222" triggers an alarm and causes a stopping of the remaining pumps by means of the controllers 206" or 225", respectively.

The pinching of a tube in the metering devices 212", 214" is recognized by means of the pressure sensors 226", 227", which transfer the signal to the controller 225" and which cause the pumps 218", 222" to stop. Via the controller 225", the signal is communicated to the controller 206", which causes the blood pump 209" to turn off.

In the event that the citrate solution of the substitution medium has been used up, the drop detectors 217", 221" trigger an alarm, which is recognized by the controller 225" and which causes the pumps 218", 222" to turn off. Via the controller 225", the signal is communicated to the controller 206", which causes the blood pump 209" to turn off.

Similar to the drop detectors 217", 221", an alarm, which is recognized by the controller 225" or the controller 206', respectively, and which is communicated to the respective other modules, is triggered by the air bubble detectors 210", 219", 223".

An alarm can further be triggered by a signal of the Ca-ion sensor 224" when—as described above—the Ca-ion concentration undershoots or exceeds a setpoint value range. A trend towards an unphysiological state is thus signalized.

An alarm can further be triggered by all other Ca-ion sensors 224', 224e, 224a, 224b, 224c, 224d, which are additionally shown in FIG. 4.

FIGS. 6a-e show different exemplary embodiments for Ca-ion sensors. To meet the high requirements on sterility, it is particularly advisable when these sensors are disposables, which are arranged at the above-mentioned positions (see FIG. 4) in the extracorporeal blood circuit or plasma circuit prior to the onset of the treatment and are disposed of after the treatment. It goes without saying that sensors, which can be sterilized, can also be used.

FIG. 6a shows a Ca-ion sensor comprising a sensor surface 600, which is integrated in a bypass line 601. A small quantity of blood is thereby branched off from the extracorporeal blood circuit 606 into the bypass line 601 and is guided onto the sensor surface 600. The branching of the blood sample takes place by means of a pump 607. Ca-sensitive molecules—for example Ca-sensitive fluorophores—which generate a signal (fluorescence signal), which corresponds to the Ca-ion concentration, are immobilized on the sensor surface 600. In the case of the ion-sensitive fluorophores, a change of the calcium concentration either leads to a change of the fluorescence intensity or to a change of the fluorescence wavelength. After the measuring, the blood sample is no longer guided back into the extracorporeal blood circuit 600, but is collected in a waste container 602 and is subsequently discarded. A valve 605a prevents a backflow of the blood sample into the extracorporeal blood circuit 606. In the event that this principle is used in the Ca-ion sensor 224 described in FIG. 2, which is arranged upstream of the citrate supply point 213, an anti-coagulation is necessary due to the low blood flow rates in the bypass line 601. This can take place by injecting anti-coagulants into the bypass line 601 via an anti-coagulant line 603. The sensor can be calibrated by means of adding a calibration solution, which is introduced into the bypass line 601 via a calibration solution line 604. Valves 605b, 605c are arranged in the anti-coagulant line 603 and in the calibration solution line 604.

FIG. 6b shows a further exemplary embodiment of a Ca-ion sensor, wherein a small quantity of blood is also branched off from the extracorporeal blood circuit 617 via a pump 618 into a bypass line 610 and the blood sample is collected in a waste container 611 and is disposed of after the measuring. Contrary to the embodiment shown in FIG. 6a, the Ca-sensitive molecules—e.g. Ca-sensitive fluorophores—are not immobilized on a sensor surface. The Ca-sensitive molecules are mixed with a blood sample, which is anti-coagulated with anti-coagulants, and the signal is detected via a detection window 612. The anti-coagulant is added to the blood sample, which is located in the bypass line 610 via an anti-coagulant line 613 and the Ca-sensitive fluorophores are added via a fluorophor line 614. The calibration solution is introduced into the bypass line 610 via a calibration solution line 615. The device elements 616a, 616b, 616c, 616d can either be valves or pumps.

FIG. 6c shows a further exemplary embodiment of a Ca-ion sensor, which encompasses a first sensor surface 630 and a second sensor surface 631. Ca-sensitive molecules—for example Ca-sensitive fluorophores—, which generate a signal (fluorescent signal), which corresponds to the Ca-ion concentration, are immobilized on the sensor surfaces 630, 631. It is possible to carry out a redundant or alternating measuring, respectively, by means of a sensor, which is embodied in such a manner. In the case of this embodiment, a small quantity of blood branches off from the extracorporeal blood circuit 639 into a bypass line 632. The bypass line 632 splits into two further bypass lines 632a and 632b. The bypass line at 632a and 632b are later reunited into a bypass line 632c, which empties into a waste container 633. In another alternative, the bypass lines 632a, 632b can also empty directly into the waste container 633 (dashed extensions). The blood reaches from the extracorporeal blood circuit 639 into the bypass line 632 via a first pump 638a and can furthermore be guided either into both bypass lines 632a and 632b or via a valve 634 either into the bypass line 632a or into the bypass line 632b. From there, the blood reaches to the respective sensor surface 631, 630. After the measuring, the blood sample is guided into the waste container 633 and is discarded. Anti-coagulant is introduced into the bypass line 632 via an anti-coagulant line 635 by means of a second pump 638b. The calibration solution is introduced into the respective bypass lines 632a, 632b via two calibration solution lines 636, 637 by means of two further pumps 638c, 638d. This configuration has the advantage that a redundant or alternating measuring is possible with only one line, which branches off from the extracorporeal blood circuit 202. In the event that the vale 634 is open for both bypass lines 632a, 632b, the blood sample flows via both sensor surfaces 630, 631 at the same time. The valve 634 can also be equipped such that the measuring can be carried out alternately, wherein the blood sample can alternately reach only into one of the bypass lines 632a, 632b and thus to the respective sensor surface 630, 631. The respective other bypass line 632a, 632b remains closed and calibration solution can be added to the respective sensor surface 630, 631.

Figure 6D:
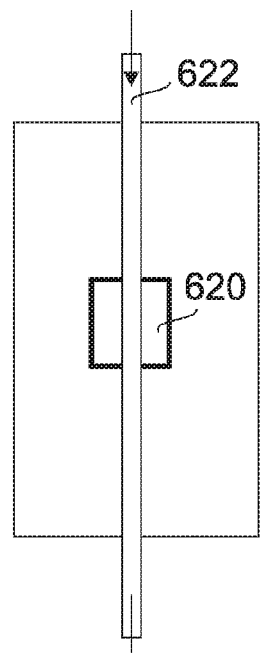

A further exemplary embodiment of a Ca-ion sensor is illustrated in FIG. 6d. Here, the sensor, which encompasses a sensor surface 620 comprising immobilized Ca-sensitive molecules—e.g. Ca-sensitive fluorophores—is arranged at the inner wall of the extracorporeal blood circuit 622. The advantage of this principle as compared to the embodiment principles in FIG. 6a, FIG. 6b and FIG. 6c is the direct measuring in the extracorporeal blood circuit 622. A bypass line is thus not necessary. The blood must not be disposed of after the measuring, but flows continuously past the sensor surface 620 located on the inner wall of the extracorporeal blood circuit. This embodiment results in high demands on the sterility and biocompatibility and the sensor should be made in such a manner that a calibration is not necessary during the duration of the treatment. As already mentioned above, the sensor known from WO 2006/029293 could also be provided with a Ca-sensitive sensor surface and could be used according to this sensor principle.

Figure 6E:
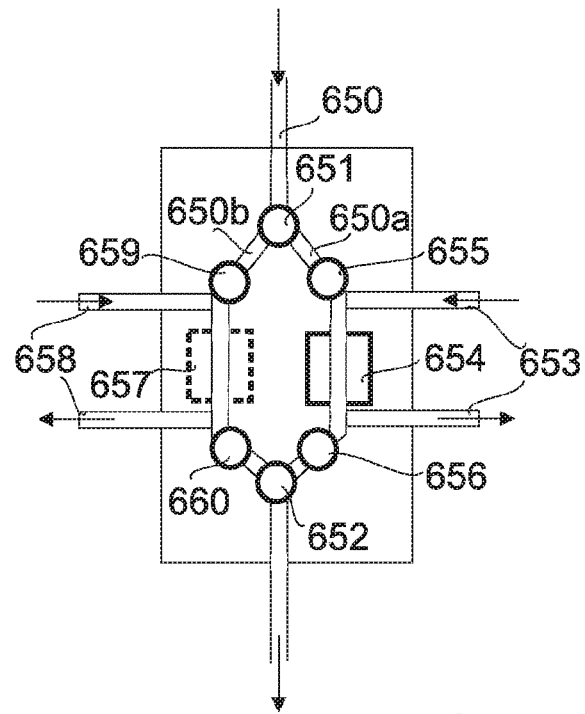

FIG. 6e shows a further exemplary embodiment of a blood-sided Ca-ion sensor, which can be recalibrated. The extracorporeal blood circuit 650 splits into two lines 650a, 650b, which later reunite into one line. Controlled by means of the valves 651, 652, the blood can thereby either flow only via one of the lines 650a, 650b or through both lines. A sensor surface 654, which is embodied according to the sensor surface 620 descried in FIG. 6c, is arranged in the line 650a. In the event that the sensor surface 654 is calibrated, the blood flows only via the line 650b. The calibration solution is guided towards the sensor surface 654 and is guided away from there again via a calibration solution line 653. Two further valves 655, 656, which are closed during this process, ensure that the calibration solution reaches into the extracorporeal blood circuit only in the area of the sensor surface. An alternating measuring is possible when a sensor surface 657 is also arranged in the line 650b. For the calibration of the sensor surface 657, provision is also made for a calibration solution line 658 and for two valves 659, 660. While the blood flows across the one sensor surface, the other sensor surface can be calibrated. Both sensor surfaces 654, 657 can be used to measure at the same time in the case of sensor surfaces, which do not require a recalibration.

It goes without saying that the exemplary embodiments illustrated in FIGS. 6a-e can also used for the Ca-ion sensors, as they are illustrated in FIG. 4.

The above-described realizations of the invention are only examples among many and are thus not to be considered to be limiting.

The invention claimed is:

1. A device for the citrate anti-coagulated extracorporeal blood purification comprising:
    an extracorporeal blood purification system comprising an extracorporeal blood circuit, which itself comprises:
        a dialysis unit;
        a blood inflow in fluid communication with an input of the dialysis unit for transporting blood drawn from a patient into said dialysis unit, and a blood discharge in fluid communication with an output of the dialysis unit for returning blood to the patient;
        a controlled citrate metering device in fluid communication with the extracorporeal blood purification system for supplying citrate, the controlled citrate metering device being disposed at a citrate supply point upstream of the dialysis unit;

a controlled substitution medium metering device in fluid communication with the dialysis unit for supplying substitution medium, the controlled substitution medium metering device being disposed at a substitution medium supply point downstream from the dialysis unit;

at least one ion concentration measuring device for measuring bivalent cations being disposed upstream of the citrate supply point, wherein the ion concentration measuring device is adapted for the continuous generation of measuring values; and a controller in signal communication with the at least one ion concentration measuring device, the citrate metering device, and the substitution medium metering device, wherein the controller is adapted to regulate the metering of the substitution medium as a function of comparison between a setpoint value range and the ion concentration measured by the at least one ion concentration measuring device disposed upstream of the citrate supply point; and wherein the controller is adapted to continuously carry out a regulation of the metering of the citrate metering device and the substitution medium metering device in consideration of one of either a target value or target value range, which is predetermined in the controller by data collected downstream from the citrate supply point and upstream of the dialysis unit.

2. The device according to claim 1, wherein the ion concentration measuring device measures alkaline earth ions.

3. The device according the claim 1, wherein the ion concentration measuring device measures calcium ions.

4. The device according to claims 1, wherein the ion concentration measuring device is an ion-sensitive sensor.

5. The device according to claim 1, wherein the ion concentration measuring device is an optical ion-sensitive sensor.

6. The device according to claim 1, wherein the ion concentration measuring device is an optical ion-sensitive sensor based on fluorescence.

7. The device according to claim 1, wherein the ion concentration measuring device is introduced into the extracorporeal blood circuit.

8. The device according to claim 1, wherein a quantity of blood is branched off from the extracorporeal blood circuit via at least one bypass line and wherein at least one ion concentration measuring device is arranging in the bypass line.

9. The device according to claim 1, further comprising an additional ion concentration measuring device downstream from the citrate supply point and upstream from of the dialysis unit.

10. The device according to claim 1, further comprising an additional ion concentration measuring device downstream from the dialysis unit and upstream of the substitution medium supply point.

11. The device according to claim 1, further comprising an additional ion concentration measuring device downstream from the substitution medium supply point.

12. The device according to claim 1, further comprising a plasma circuit comprising an additional ion concentration measuring device.

13. The device according to claim 1, wherein the citrate and substitution medium metering devices and the extracorporeal blood purification system are connected to one another via the controller by means of a plurality of signal connections, wherein the controller is adapted to include signals from extracorporeal blood purification system in its regulation.

14. The device according to claim 1, wherein the citrate and substitution medium metering devices and the extracorporeal blood purification system are connected to one another via the controlled by means of a plurality of signal connections, wherein the controller is adapted to include signals from the metering devices in its regulation.

15. The device according to claim 1 further comprising a filtration device for the extracorporeal blood purification system, wherein the citrate and substitution medium metering devices and the extracorporeal blood purification system are connected to one another via the controller by means of a plurality of signal connections, and wherein the controller is adapted to one of either initiate proportional change of to the ultrafiltration quantity of the filtration device or provide an indicator to an operator in response to a change in at least one of the citrate supply rate and the substitution medium supply rate.

* * * * *